(12) United States Patent
Han et al.

(10) Patent No.: US 11,311,466 B2
(45) Date of Patent: Apr. 26, 2022

(54) OIL-IN-WATER EMULSION COMPOSITION, PREPARATION METHOD THEREFOR AND PRODUCT

(71) Applicant: Shiseido Company, Ltd., Tokyo (JP)

(72) Inventors: Yang Han, Beijing (CN); Reiji Miyahara, Tokyo (JP); Ying Wang, Beijing (CN)

(73) Assignee: Shiseido Company, Ltd., Tokyo (JP)

( * ) Notice: Subject to any disclaimer, the term of this patent is extended or adjusted under 35 U.S.C. 154(b) by 103 days.

(21) Appl. No.: 16/651,848

(22) PCT Filed: Sep. 28, 2018

(86) PCT No.: PCT/CN2018/108309
§ 371 (c)(1),
(2) Date: Mar. 27, 2020

(87) PCT Pub. No.: WO2019/062845
PCT Pub. Date: Apr. 4, 2019

(65) Prior Publication Data
US 2020/0246230 A1    Aug. 6, 2020

(30) Foreign Application Priority Data
Sep. 29, 2017    (CN) .......................... 201710912334.X

(51) Int. Cl.
*A61K 8/06* (2006.01)
*A61K 8/34* (2006.01)
*A61K 8/73* (2006.01)
*A61K 8/92* (2006.01)

(52) U.S. Cl.
CPC ................ *A61K 8/062* (2013.01); *A61K 8/34* (2013.01); *A61K 8/731* (2013.01); *A61K 8/92* (2013.01); *A61K 2800/10* (2013.01)

(58) Field of Classification Search
CPC .......... A61K 8/062; A61K 8/34; A61K 8/731; A61K 8/92; A61K 2800/10; A61K 8/342; A61Q 19/00
See application file for complete search history.

(56) References Cited

U.S. PATENT DOCUMENTS

| | | | |
|---|---|---|---|
| 9,119,785 B2 | 9/2015 | Nguyen et al. | |
| 2009/0047226 A1* | 2/2009 | Teckenbrock | A61K 8/062 424/59 |
| 2013/0244976 A1 | 9/2013 | Inamoto et al. | |
| 2015/0297475 A1 | 10/2015 | Hiki | |
| 2017/0172888 A1 | 6/2017 | Tashiro et al. | |

FOREIGN PATENT DOCUMENTS

| | | | | |
|---|---|---|---|---|
| CN | 102348451 A | 2/2012 | | |
| CN | 103118660 A | 5/2013 | | |
| CN | 104135998 A | 11/2014 | | |
| CN | 106572958 A | 4/2017 | | |
| JP | 2016-117673 A | 6/2016 | | |
| WO | WO-2010103008 A1 * | 9/2010 | ............... A61K 8/14 |

OTHER PUBLICATIONS

Tanaka et al. (JP2012140385A Machine Translation) (Year: 2012).*

* cited by examiner

*Primary Examiner* — Robert A Wax
*Assistant Examiner* — Quanglong N Truong
(74) *Attorney, Agent, or Firm* — Foley & Lardner LLP

(57) ABSTRACT

Disclosed is an oil-in-water emulsion composition, and a preparation method therefor, and a product, wherein the composition comprises: a) cellulose with a hydrophobic group; b) a surfactant; c) a higher alcohol; d) an oil component; e) water; and optionally, f) a humectant and/or g) a higher fatty acid; the composition has a viscosity of 10,000 mPa·s or less.

14 Claims, No Drawings

OIL-IN-WATER EMULSION COMPOSITION, PREPARATION METHOD THEREFOR AND PRODUCT

TECHNICAL FIELD

The present disclosure belongs to the field of daily chemical industry, particularly relates to the field of cosmetics, and especially to an oil-in-water emulsion composition, a preparation method therefor, and a product.

BACKGROUND

An oil-in-water composition is a common source used in the cosmetic industry to prepare products, such as emulsions, nourishing water, essences and floral water. In the oil-in-water composition, an oil phase ingredient exists evenly and stably in an aqueous system under the action of surfactants. Such a system can be transparent, translucent, or opaque, depending on the size of oil phase droplets dispersed in the dispersion system. In addition, it is also possible to achieve a stable equilibrium between the continuous phase and the oil phase in the dispersion system with the aid of external shear forces or ultrasonic waves or other means.

During storage, transportation and use, ordinary oil-in-water emulsions and microemulsions suffer from a shear force for a long time, which may lead to a significant decrease in the stability of their systems, thereby affecting the appearance and sensation during use of cosmetics. Although the shear force may not be very violent in a certain instance, due to frequent exposure to such a shearing effect, for example, during the use of a cosmetic containing the oil-in-water emulsion, because of possibly frequent shearing effects on unused emulsion in a container, the stability of the emulsion in the container may be greatly decreased, thereby affecting the appearance and sensation during use of the unused emulsion.

In Literature 1, disclosed is α-gel formed of a higher aliphatic alcohol, an anionic surfactant and water, and a cationic surfactant is added to improve the stability over time of the α-gel, but it does not concern a change in viscosity of the emulsified composition undergoing a shear force.

In Literature 2, disclosed is a hair treatment composition, comprising 0.1 to 1% associative polymer, a cationic surfactant, and 0.5 to 5% higher alcohol, and further comprising an anionic surfactant, PEG-60 hydrogenated castor oil and water. The hair treatment composition exhibits enough stability during storage and dispensing while at the same time this interaction is weak enough to be broken down under the shear forces during application to the hair. So, it provides a product which is easy to work through the hair.

Therefore, in cosmetics, especially in skin care emulsion cosmetics, there is still a need for further increased or improved shear resistance and stability at present.

CITATION LIST

Patent Literature

Cited Literature 1: CN 102791247 A
Cited Literature 2: CN 1377250 A

SUMMARY

Problem to be Solved by the Invention

In consideration of the above deficiencies mentioned in the prior art, the present disclosure provides an oil-in-water emulsion composition having excellent shear resistance during storage, transportation and use, while exhibiting pleasant texture and coating easiness during use.

Besides, another object of the present disclosure is to provide a method for preparing an oil-in-water emulsion composition having excellent shear resistance, and a cosmetic containing this composition, wherein the cosmetic includes skin care cosmetics or hair treatment cosmetics.

Means for Solving the Problem

The present disclosure first provides an oil-in-water emulsion composition, wherein the composition comprises:
a) cellulose with a hydrophobic group;
b) a surfactant;
c) a higher alcohol;
d) an oil component;
e) water;
and optionally, f) a humectant and/or g) a higher fatty acid;
the composition has a viscosity of 10,000 mPa·s or less.

The composition according to the foregoing, wherein the content of the a) component is from 0.02 to 0.1 mass % as per a total mass of the composition.

The composition according to the foregoing, wherein the composition has a viscosity of 2,000 mPa·s (at 30° C.) or more.

The composition according to any one of the foregoing, the a) component refers to cellulose hydrophobically modified with long-chain alkyl having, preferably, 12 to 22 carbon atoms.

The composition according to any one of the foregoing, having either of the following characteristics:
i) when the composition is subjected to a rolling test carried out at 45 r/min for 4 h, the viscosity of the composition measured at the end of the test decreases by less than 10%, as compared with the initial viscosity thereof; and
ii) when the composition is subjected continuously to a rolling test carried out at 45 r/min for 4 h and a vibration test carried out at a frequency of 270 times/min for 20 min, the viscosity of the composition measured at the end of the test decreases by less than 20%, as compared with the initial viscosity thereof.

The composition according to any one of the foregoing, wherein the surfactant is a non-ionic surfactant.

In addition, the present disclosure further provides a cosmetic, comprising a composition according to any one of the foregoing.

Effects of the Invention

The oil-in-water emulsion composition provided herein as a cosmetic product has the following excellent effects:
(1) during storage, transportation and use, the shear resistance is good; the emulsion is basically stable; and the flow state of the system does not change significantly;
(2) the viscosity of the oil-in-water emulsion composition is kept at 10,000 mPa·s (at 30° C.) or less, and it does not cause sticky feeling when coated on skin; and
(3) when used as a raw material or component of a cosmetic, the oil-in-water emulsion composition according to the present disclosure is easily produced, namely, it is well economic, while gaining excellent shear resistance and human body feeling as described above.

DETAILED DESCRIPTION

The oil-in-water emulsion composition provided herein comprises, as five essential components, a) cellulose with a hydrophobic group, b) a surfactant, c) a higher alcohol, d) an oil component, and e) water, and comprises f) a humectant and/or g) a higher fatty acid as optional component(s).

Typically, a mixture of (b)+(c)+(d)+(e), which is obtained by dissolving a surfactant and a higher alcohol in an oil phase respectively, mixing and emulsifying the two phases, and then getting the higher alcohol dispersed in the water phase, may not be stable enough, and when the mixture is subjected to a shear force, its viscosity reduces accordingly, which is not conducive to long-term storage, transportation and use of the mixture.

In the present disclosure, the oil-in-water emulsion composition contains a) cellulose with a hydrophobic group, which has a lower content, e.g., 0.02 to 0.1 mass %. As a result, in one aspect, the a) cellulose with a hydrophobic group endows the oil-in-water emulsion composition with excellent shear resistance, so that the system stability does not change significantly and the uniformity of the emulsion remains good during storage and use of the oil-in-water emulsion composition under a long period of shear forces; in the other aspect, the viscosity of the oil-in-water emulsion composition can be controlled at 10,000 mPa·s or less, which causes no adverse effect on the sensation during use but is easy to coat when a cosmetic product containing the oil-in-water emulsion composition according to the present disclosure is coated on human body.

Hereinafter, various components used in the present disclosure will be described in detail. It should be noted that unless otherwise stated, the units used below are international standard units; besides, all of the viscosity data in the present application are those measured at room temperature, or more specifically, those measured at 30° C. for example. In addition, the "percent content" or "%" used below means a mass percentage content or "mass %".

<a) Cellulose with Hydrophobic Group>

The a) component refers to cellulose hydrophobically modified with long-chain alkyl having, preferably, 12 to 22 carbon atoms.

In the prior art, cellulose-based polymers are generally used as thickeners, as they can increase the viscosity of cosmetics. Examples of cellulose polymers that can be used as thickeners include: methyl cellulose, ethyl cellulose, hydroxypropyl methyl cellulose, hydroxyethyl cellulose, sodium cellulose sulfates, dialkyldimethyl ammonium sulfate cellulose, hydroxypropyl cellulose, carboxymethyl cellulose, and the like. However, not all of cellulosic thickeners having high molecular weights as used in the prior art meet the requirements of the present disclosure.

If cellulose that is not hydrophobically modified is in lieu of the a) component of the present disclosure, the resulting emulsion composition does not have a satisfactory capability of resisting shear forces, and suffers a greater viscosity reduction rate under a certain shear force during use, storage or transportation, so the stability of the emulsion composition cannot be maintained.

In a preferred embodiment of the present disclosure, cellulose hydrophobically modified with long-chain alkyl having 12 to 22 carbon atoms is hydroxypropyl methylcellulose stearoxy ether (Sangelose®). The stearoxy is linked to cellulose monomeric unit ($-OCH_2CH(OH)CH_2OC_{18}H_{37}$) via hydroxypropoxy. In some embodiments of the present disclosure, it is preferred that the hydrophobically modified cellulose has a kinematic viscosity of greater than 120 $mm^2/s$.

Examples of suitable commercial products that can be applied in the present disclosure include: Sangelose 90L, Sangelose 60L, Sangelose 90M, Sangelose 60M, Sangelose 90H, Sangelose 60H, all of which have different stearoxy content. According to the present disclosure, Sangelose 90L is preferable, and Sangelose 90L contains 0.3 to 0.6 mass % of stearoxy hydroxypropoxy as per a total mass of the hydroxypropyl methylcellulose stearoxy ether.

In a preferred embodiment of the present disclosure, as per a total mass of the oil-in-water emulsion composition, the a) cellulose with a hydrophobic group has a content of from 0.02 to 0.1 mass %, preferably from 0.02 to 0.09 mass %, more preferably from 0.03 to 0.08 mass %, more preferably from 0.04 to 0.06 mass %, most preferably from 0.02 to 0.04 mass %.

In the present disclosure, the weight-average molecular weight (Mw) of the a) cellulose with a hydrophobic group is not particularly limited. The weight-average molecular weight (Mw) of the cellulose with a hydrophobic group has no significant influence on the shear resistance of the composition, and it may be tens of thousands, hundreds of thousands or millions of molecular weight.

Further, in order to check the shear resistance performance of the composition, a rolling test and a vibration test have been simulated. In a preferred embodiment, the composition meets either of the following conditions:

i) when the composition is subjected to a rolling test carried out at 45 r/min for 4 h, the viscosity of the composition measured at the end of the test decreases by less than 10%, preferably less than 8%, more preferably less than 5%, more preferably less than 2%, more preferably less than 1%, as compared with the initial viscosity thereof; and ii) when the composition is subjected continuously to a rolling test carried out at 45 r/min for 4 h and a vibration test carried out at a frequency of 270 times/min for 20 min, the viscosity of the composition measured at the end of the test decreases by less than 20%, preferably less than 20%, more preferably less than 10%, more preferably less than 5%, more preferably less than 3%, more preferably less than 1%, as compared with the initial viscosity thereof.

The initial viscosity here indicates the viscosity tested after one-day storage of the prepared composition.

<b) Surfactant>

The surfactant used in the present disclosure is not particularly limited as long as it is usable in the field of cosmetics, including: a cationic surfactant, an anionic surfactant, a zwitterionic surfactant, a non-ionic surfactant.

Examples of the cationic surfactant used in the present disclosure include fatty acid soaps, higher alkyl sulfates, alkyl ether sulfates, N-acylsarcosines, higher fatty acid amide sulfonates, phosphates, sulfonic succinates, alkyl benzene sulfonates, higher fatty acid ester sulfates, N-acyl glutamates, POE-alkylether carboxylic acids, POE-alkylarylether carboxylates, α-olefin sulfonates, higher fatty acid ester sulfonates, sec-alcohol sulfates, higher fatty acid alkylamide sulfates, sodium lauroyl monoethanolamine succinates, ditriethanolamine N-palmitoylaspartates, sodium caseinates, etc.

Examples of the anionic surfactant used in the present disclosure include alkyltrimethylammonium salts, alkylpyridinium salts, di stearyldimethylammonium chlorides, dialkyldimethylammonium salts, alkyl quaternary ammonium salts, alkyl dimethylbenzyl ammonium salts, POE-alkyl amines, alkyl amine salts, polyamine fatty acid derivatives, amylalcohol fatty acid derivatives, etc.

Examples of the zwitterionic surfactant used in the present disclosure include amino acid-type zwitterionic surfactants (such as lauraminopropionic acid), carboxylic acid betaines (such as alkyl dimethyl betaine), sulfobetaines (such as alkyl dimethyl sulfoethyl betaine, alkyl dimethyl sulfopropyl betaine), phosphate betaines (such as alkyl dimethylhydroxypropyl phosphate betaine), imidazoline-type zwitterionic surfactants, etc.

In the present disclosure, the non-ionic surfactant is preferred. Examples of the non-ionic surfactant used in the present disclosure include polyoxyethylene fatty acid glycerides, polyoxyethylene-polymethylsiloxane copolymers, polyoxyethylene sorbitan fatty acid esters, polyoxyethylene alkyl ethers, maltitol hydroxy aliphatic alkyl ethers, alkylation polysaccharides, alkyl glycosides, sucrose fatty acid esters, etc.

In the present disclosure, a mixture of one or two or more kinds of the above-mentioned surfactants may be used as the b) component.

In consideration of stability maintenance and sensation during use, in some preferred embodiments of the present disclosure, the surfactant is preferably a non-surfactant, as it surprisingly shows better system stability than other kinds of surfactants.

In other preferred embodiments of the present disclosure, when two or more kinds of the surfactants are used, a usage amount of the non-ionic surfactant accounts for 50 mass % or more, preferably 60 mass % or more, more preferably 70 mass % or more of the total usage amount of the surfactants.

<c) Higher Alcohol>

The higher alcohol used in the present disclosure is not particularly limited, as long as it can be used in the field of cosmetics. Examples of the higher alcohol used in the present disclosure include behenyl alcohols, batilols, hexadecanols, stearyl alcohols, etc.

In the present disclosure, a mixture of one or two or more kinds of the above-mentioned higher alcohols may be used as the c) component.

<d) Oil Component>

In the present disclosure, there is no particular limitation on the oil component that can be formulated as an internal phase of the emulsion composition, as long as it can dissolve the c) higher alcohol.

As an oil component, it can be selected from substances commonly used in cosmetics within a range that does not adversely affect stability. Examples of preferable oil components include hydrocarbon oils, liquid oils and fats, ester oils, and silicone oils, and the like.

As hydrocarbon oil, it can be liquid paraffin, squalane, squalene, paraffin, isoparaffin, ceresin, vaseline, hydrogenated polydecene, and the like.

Examples of the silicone oils include chain-like organosilicones, such as methylphenyl polysiloxane and methyl hydrogen polysiloxane; silicone resins, silicone rubbers, etc. having a three-dimensional network structure.

Examples of the liquid fats and oils include palm oil, palm nut oil, linseed oil, camellia oil, macadamia nut oil, corn oil, mink oil, olive oil, avocado oil, sasanqua oil, castor oil, safflower oil, jojoba oil, sunflower oil, almond oil, rapeseed oil, sesame oil, soybean oil, peanut oil, triglycerin, glycerin trioctanoate, and glycerin triisopalmitate.

Examples of ester oil include hexanoic acid 2-ethylhexadecyl ester, hexyl laurates, isopropyl myristates, octyl palmitates, isocetyl stearates, isopropyl stearates, isooctyl palmitates, isodecyl oleates, cetyl ethyl hexanoates, tri(2-ethylhexoic acid)glycerides, tetra(2-ethylhexanoate)pentaerythritols, 2-ethylhexyl succinates, diethyl sebacates, and so on.

Evidently, the upper limit on the usage amount of these additional oil components is the one that does not adversely affect the technical effects of the present disclosure.

<e) Water>

It goes without saying that the continuous phase in the oil-in-water system of the present disclosure is an aqueous phase, and the water in the present disclosure may be distilled water, ion exchange water, or various other purified water. The water is compounded and used in such an amount, relative to the usage amount of the whole oil-in-water emulsion composition, that enables the whole composition is up to a full amount of 100%.

<Preparation Method for Oil-In-Water Emulsion Composition>

The oil-in-water emulsion composition in the present disclosure can be manufactured by those methods that are commonly used to manufacture emulsions, and can be manufactured by, for example, formulating an oil phase component and an aqueous phase component respectively, mixing the oil phase and the aqueous phase, and emulsifying them with a diffuser or homogenizer or the like.

In the presence of the essential components described above in the present disclosure, the method for forming the oil-in-water emulsion system of the present disclosure is not specially limited. It is possible to utilize mechanical agitation to provide a necessary mixed shear force, or to mix the oil phase component and the aqueous phase component by ultrasonic processing to obtain a stable emulsion.

Likewise, a device for preparing the oil-in-water emulsion composition of the present disclosure is not particularly limited as long as it is up to the above demands.

The oil-in-water emulsion composition of the present disclosure may be in an emulsion state, and may be translucent or opaque.

Out of production and usage, the oil-in-water emulsion composition obtained in the present disclosure has a viscosity of 10,000 mPa·s (at 30° C.) or less and 2,000 mPa·s or 3,000 mPa·s (at 30° C.) or more, so as to maintain good sensation during use without sticky feeling and to provide customers with refreshing skin feeling, and further preferably has a viscosity of 4,000 to 9,000 mPa·s (at 30° C.). If the viscosity is too low, it may influence the using effect of the product; if the viscosity is too high, such a concern about adverse effects on coating and sensation during use will arise.

<Other Additives>

As unnecessary ingredients of the oil-in-water emulsion composition in the present disclosure, a variety of other components or functional ingredients conventionally used in this field can be added, and there is no limitation on them as long as they do not destroy the above effects of the present disclosure.

The optional components included in the oil-in-water emulsion composition of the present disclosure are f) a humectant and/or g) a higher fatty acid.

Examples of the f) humectant include glycerin, 1,3-butylene glycol, propylene glycol, dipropylene glycol, polyethylene glycol-based humectants, hyaluronic acid (HA), sodium pyrrolidone carboxylate (PCA-NA), ceramide, collagen, urea, lactic acid, chitin derivatives, aloe, alga extract, etc. One or two or more kinds of these humectants may be combined for compounding.

Examples of the g) higher fatty acid include behenic acid, isostearic acid, stearic acid, oleic acid, linoleic acid, linolenic acid, lauric acid, myristic acid, palmitic acid, 12-hydroxystearic acid, undecylenic acid, tallic acid, eicosapentaenoic acid (EPA), docosahexaenoic acid (DHA), etc. One or two or more kinds of these higher fatty acids may be combined for compounding.

The compounding amount of the f) humectant and/or the g) higher fatty acid in the present disclosure is the one commonly used in emulsified cosmetics.

In addition, without an influence on the effects (including stability and sensation during use) of the present disclosure, the oil-in-water emulsion composition of the present disclosure may further comprise other water-soluble thickeners, and examples of the water-soluble thickener may include plant-based polymers such as gum Arabic, gum tragacanth, galactosan, guar gum, carrageenan, pectin, marmelo extract, and phaeophyta powder, microorganism-based polymers such as xanthan gum, glucan, Pulullan, and succinoglycan, animal-based polymers such as collagen, casein, albumin, and gelatin; starches such as carboxymethyl starch and hydroxymethyl starch, cellulose such as methylcellulose, nitroncellulose, ethyecellulose, methylhydroxypropyl cellulose, hydroxyethyl cellulose, cellulose sulfate, hydroxypropyl cellulose, carboxymethyl cellulose, crystalline cellulose, and powdered cellulose, vinyl polymers such as polyvinylalcohol, polyvinyl methyl ether, polyvinylpyrrolidone, and carboxyvinyl polymers, acrylic acid-based polymers such as polyacrylamide, and (dimethylacrylamide/sodium acryloyldimethyltaurate)cross polymers, and glycyrrhizic acid, alginic acid and salts thereof, etc. Of note, although the above conventional thickeners used in this field are capable of stabilizing the system, in fact, accompanied is an effect of lowered sensation during use, and in particular, it is easy to cause sticky feeling during use of products such as cosmetics, which is disadvantageous. Therefore, in a preferred embodiment of the present application, when other thickeners described above than the a) component of the present application is used, the usage amount of the above thickeners accounts for 30 mass % or less, preferably 20 mass % or less, more preferably 10 mass % or less of the weight of the a) component. In the most preferred embodiment of the present disclosure, the other thickeners than the a) component is not used.

Besides, various ingredients, e.g., skin conditioners, stabilizers, preservatives, metal ion chelating agents, pigments, pH adjusters, skin nutrients, vitamins, preservatives, antioxidants, antioxidant assistants, perfumes, etc., that are commonly used in the fields of cosmetics and medicine can be appropriately compounded when necessary.

Examples of various additives may further include whitening additives, anti-aging additives, anti-acne additives, UV-protective additives, various applicable plant essences or plant extracts, etc.

Additionally, inorganic functional additives, such as silica and mica, can also be added according to the needs of cosmetic products.

<Cosmetics>

In particular, the present disclosure also provides a cosmetic containing the oil-in-water emulsion composition as described above. The kind of the cosmetic is not particularly limited in the present disclosure, and mainly includes skin care cosmetics, hair treatment cosmetics, and so on. The products thereof may be emulsions, essences, floral water or other similar products, etc.

EXAMPLES

The present disclosure will be further described by referring to the following specifically preferred examples. In particular, the implementation of the present disclosure is not limited to these examples, and further, the following specific examples do not intend to limit the inventions of the present disclosure.

(I) Examples 1 and 2 and Comparative Examples 1 to 9

Oil-in-water emulsion compositions were formed as per the following specific formulae listed in Table 1 to obtain Examples 1 and 2, in which the cellulose with a hydrophobic group was hydroxypropyl methylcellulose stearoxy ether, and had a kinematic viscosity of greater than 120 (mm$^2$/s).

On the basis of Example 1 or Example 2, the a) component as a single variable was changed to get Comparative Examples 1 to 9, and the specific formulae thereof were listed in Tables 1 to 3. In view of this, the effects of the kind and content of the a) component in the present disclosure on the emulsion composition were discussed. Among them, Comparative Example 1 was obtained by adjusting the content of the a) component based on Example 1 or 2;

Comparative Examples 2 to 7 and Comparative Example 9 were obtained by changing the kind of the a) component based on Example 2; and Comparative Example 8 was obtained by changing the kind of the a) component based on Example 1.

Furthermore, all indices in Examples 1 and 2 and Comparative Examples 1 to 9 as mentioned above were tested, and the test results were listed in Tables 1 to 3.

Rolling test condition: the emulsion was put in a glass bottle, and the glass bottle was placed horizontally and rolled at 45 r/min for 4 h.

Vibration test condition: the emulsion was put in a glass bottle, and the glass bottle was placed vertically and vibrated 270 times/min for 20 min.

The term "viscosity/1 day" indicates the viscosity datum measured (with a B-type viscometer, at 30° C.) after one day storage of the samples prepared in the Examples and Comparative Examples.

Viscosity reduction rate: it is a value resulting from the following equation: (the viscosity of a sample subjected to a rolling test and a vibration test—the viscosity of the sample stored for one day after preparation)/the viscosity of the sample stored for one day after preparation.

TABLE 1

| Name of Raw Material | Comparative Example 1 | Example 1 Hundreds of thousands Molecular Weight (Mw) With hydrophobic group | Example 2 |
|---|---|---|---|
| a) Component | | | |
| Water | 75.6270 | 75.6070 | 75.5270 |
| Humectant | 11.000 | 11.000 | 11.000 |
| Hydroxypropyl methylcellulose stearoxy ether | — | 0.020 | 0.100 |
| PEG-240/HDI copolymer bis-decyltetradeceth-20 ether | | | |
| Polyethylene glycol-20000 | | | |
| Hydroxypropyl cellulose | | | |
| Hydroxyethyl cellulose | | | |
| Hydroxypropyl methyl cellulose | | | |
| Acrylates/C10-30 alkyl acrylate cross polymer | | | |
| Carbomer | | | |
| Potassium hydroxide | 0.060 | 0.060 | 0.060 |
| Behenic acid | 0.300 | 0.300 | 0.300 |
| PEG-10 polydimethylsiloxane | 0.300 | 0.300 | 0.300 |
| PEG-60 glyceryl isostearate | 0.300 | 0.300 | 0.300 |

TABLE 1-continued

| Name of Raw Material | Comparative Example 1 | Example 1 Hundreds of thousands Molecular Weight (Mw) With hydrophobic group | Example 2 |
|---|---|---|---|
| Behenyl alcohol | 1.650 | 1.650 | 1.650 |
| Batilol | 0.450 | 0.450 | 0.450 |
| Oil component | 6.100 | 6.100 | 6.100 |
| Skin conditioner | 3.500 | 3.500 | 3.500 |
| Stabilizer | 0.213 | 0.213 | 0.213 |
| Preservative | 0.500 | 0.500 | 0.500 |
| Total | 100.0000 | 100.0000 | 100.0000 |
| Test | | | |
| Viscosity/1 day | 4520 | 5680 | 9700 |
| Rolling test + vibration test | 3400 | 5520 | 9670 |
| Viscosity reduction rate | 24.78% | 2.82% | 0.31% |

TABLE 2

| Name of Raw Material | Comparative Example 2 Tens of thousands Mw With hydrophobic group | Comparative Example 3 Tens of thousands Mw Without hydrophobic group | Comparative Example 4 Hundreds of thousands Mw Without hydrophobic group | Comparative Example 5 Hundreds of thousands Mw Without hydrophobic group |
|---|---|---|---|---|
| a) Component | | | | |
| Water | 75.5270 | 75.5270 | 75.5270 | 75.5270 |
| Humectant | 11.000 | 11 | 11 | 11 |
| Hydroxypropyl methylcellulose stearoxy ether | | | | |
| PEG-240/HDI copolymer bis-decyltetradeceth-20 ether | 0.1 | | | |
| Polyethylene glycol-20000 | | 0.1 | | |
| Hydroxyethyl cellulose | | | 0.1 | |
| Hydroxypropyl methyl cellulose | | | | 0.1 |
| Acrylates/C10-30 alkyl acrylate cross polymer | | | | |
| Carbomer | | | | |
| Potassium hydroxide | 0.060 | 0.060 | 0.060 | 0.060 |
| Behenic acid | 0.300 | 0.300 | 0.300 | 0.300 |
| PEG-10 polydimethylsiloxane | 0.300 | 0.300 | 0.300 | 0.300 |
| PEG-60 glyceryl isostearate | 0.300 | 0.300 | 0.300 | 0.300 |
| Behenyl alcohol | 1.650 | 1.650 | 1.650 | 1.650 |
| Batilol | 0.450 | 0.450 | 0.450 | 0.450 |
| Oil component | 6.100 | 6.100 | 6.100 | 6.100 |
| Skin conditioner | 3.500 | 3.500 | 3.500 | 3.500 |
| Stabilizer | 0.213 | 0.213 | 0.213 | 0.213 |
| Preservative | 0.500 | 0.500 | 0.500 | 0.500 |
| Total | 100.0000 | 100.0000 | 100.0000 | 100.0000 |
| Test | | | | |
| Viscosity/1 day | 5030 | 4430 | 4220 | 3720 |
| Rolling test + vibration test | 2550 | 2220 | 1740 | 1900 |
| Viscosity reduction rate | 49.30% | 49.89% | 58.77% | 48.92% |

TABLE 3

| Name of Raw Material | Comparative Example 6 Millions Mw With hydrophobic group | Comparative Example 7 Millions Mw With hydrophobic group | Comparative Example 8 Millions Mw Without hydrophobic group |
|---|---|---|---|
| a) Component | | | |
| Water | 75.5270 | 75.6070 | 75.5270 |
| Humectant | 11 | 11 | 11 |
| Hydroxypropyl methylcellulose stearoxy ether | | | |
| PEG-240/HDI copolymer bis-decyltetradeceth-20 ether | | | |

TABLE 3-continued

|  | Comparative Example 6 | Comparative Example 7 Millions Mw | Comparative Example 8 |
| --- | --- | --- | --- |
| Name of Raw Material | | With hydrophobic group | Without hydrophobic group |
| Polyethylene glycol-20000 | | | |
| Hydroxypropyl cellulose | | | |
| Hydroxyethyl cellulose | | | |
| Hydroxypropyl methyl cellulose | | | |
| Acrylates/C10-30 alkyl acrylate cross polymer | 0.1 | 0.02 | |
| Carbomer | | | 0.1 |
| Potassium hydroxide | 0.060 | 0.060 | 0.060 |
| Behenic acid | 0.300 | 0.300 | 0.300 |
| PEG-10 polydimethylsiloxane | 0.300 | 0.300 | 0.300 |
| PEG-60 glyceryl isostearate | 0.300 | 0.300 | 0.300 |
| Behenyl alcohol | 1.650 | 1.650 | 1.650 |
| Batilol | 0.450 | 0.450 | 0.450 |
| Oil component | 6.100 | 6.100 | 6.100 |
| Skin conditioner | 3.500 | 3.500 | 3.500 |
| Stabilizer | 0.213 | 0.213 | 0.213 |
| Preservative | 0.500 | 0.500 | 0.500 |
| Total | 100.0000 | 100.0000 | 100.0000 |
| Test | | | |
| Viscosity/1 day | 10850 | 4040 | 5780 |
| Rolling test + vibration test | 10650 | 1930 | 3520 |
| Viscosity reduction rate | 1.84% | 52.23% | 39.10% |

The above test results show:

In Comparative Example 1, the content of the a) component is 0, which is a blank control group; the initial viscosity of the obtained emulsion composition is acceptable, but its viscosity reduction rate after the rolling test and vibration test is greater than 20% as limited in the present disclosure, and the effect is unsatisfactory, so Comparative Example 1 is excluded from the scope of the present disclosure.

However, when the a) component is cellulose without a hydrophobic group (Comparative Examples 4 and 5), a lack of modification with a hydrophobic group may cause the initial viscosity of the oil-in-water system to be significantly reduced, and the viscosity reduction rate also reduces greatly, so this situation is excluded from the scope of the present disclosure.

When the a) components of Comparative Examples 2 and 3 and Comparative Examples 6 to 8 are non-cellulosic materials, it can be seen that regardless of whether or not there is a hydrophobic group, each of the Comparative Examples after replacement cannot obtain satisfactory system stability. Among these comparative examples, although Comparative Example 6 shows excellent shear resistance, its viscosity is too large and exceeds 10,000 mPa·s as limited in the present disclosure, which may affect the sensation during use and bring on stickiness and uncomfortable feeling.

(II) Examples 3 and 4 and Comparative Example 9

Oil-in-water emulsion compositions were prepared in the same manner as (I). Unlike Examples 1 and 2, the kinematic viscosities of the hydroxypropyl methylcellulose stearoxy ether used in Examples 3 and 4 were less than 110 (mm$^2$/s). Besides, Comparative Example 9 did not utilize cellulose with a hydrophobic group.

The components and test results of the compositions are listed in Table 4.

It can be seen from Table 4 that because Comparative Example 9 does not contain cellulose with a hydrophobic group, its system stability deteriorates significantly in the tests.

TABLE 4

| Name of Raw Material | Comparative Example 9 | Example 3 | Example 4 |
| --- | --- | --- | --- |
| Water | 75.6270 | 75.6070 | 75.5870 |
| Humectant | 11.000 | 11.000 | 11.000 |
| Hydroxypropyl methylcellulose stearoxy ether | | 0.020 | 0.040 |
| Potassium hydroxide | 0.060 | 0.060 | 0.060 |
| Behenic acid | 0.300 | 0.300 | 0.300 |
| PEG-10 polydimethylsiloxane | 0.300 | 0.300 | 0.300 |
| PEG-60 glyceryl isostearate | 0.300 | 0.300 | 0.300 |
| Behenyl alcohol | 1.650 | 1.650 | 1.650 |
| Batilol | 0.450 | 0.450 | 0.450 |
| oil component | 6.100 | 6.100 | 6.100 |
| Skin conditioner | 3.500 | 3.500 | 3.500 |
| Stabilizer | 0.213 | 0.213 | 0.213 |
| Preservative | 0.500 | 0.500 | 0.500 |
| Total | 100.0000 | 100.0000 | 100.0000 |
| Test | | | |
| Viscosity/1 day | 5979 | 6799 | 6719 |
| Rolling test + vibration test | 2010 | 5569 | 5639 |
| Viscosity reduction rate | 66.38% | 18.09% | 16.07% |

(III) Example 5 and Comparative Example 10

Oil-in-water emulsion compositions were prepared in the same manner as (I), except that in Example 5, a cationic surfactant was in lieu of the non-ionic surfactant in Examples 1 and 2.

Besides, Comparative Example 10 did not employ cellulose with a hydrophobic group.

The components and test results of the compositions are listed in Table 5.

Table 5 shows that due to the absence of cellulose with a hydrophobic group in Comparative Example 10, its system stability deteriorates significantly in the tests.

TABLE 5

| Name of Raw Material | Comparative Example 10 | Example 5 |
| --- | --- | --- |
| Oil component | 5 | 5 |
| Cetanol | 0.2 | 0.2 |
| Stearyl alcohol | 2.5 | 2.5 |
| Humectant | 5.5 | 5.5 |
| Octadearyl dimethyl ammonium chloride | 1.93 | 1.93 |
| Hydroxypropyl methylcellulose stearoxy ether | — | 0.02 |
| Stabilizer | 0.06 | 0.06 |
| Preservative | 0.5 | 0.5 |
| Water | 84.31 | 84.29 |
| Total | 100.00000 | 100.00000 |
| Test | | |
| Viscosity/1 day | 3989 | 3229 |
| Rolling test + vibration test | 1810 | 2929 |
| Viscosity reduction rate | 54.62% | 9.29% |

INDUSTRIAL APPLICABILITY

The oil-in-water emulsion composition involved in the present disclosure can be prepared in industrial production, and can also be used for cosmetic products.

What is claimed is:

1. An oil-in-water emulsion composition, wherein the composition comprises:
   a) cellulose with a hydrophobic group;
   b) a surfactant;
   c) a higher alcohol;
   d) an oil component;
   e) water;
   and optionally, f) a humectant, and/or g) a higher fatty acid;
   the composition has a viscosity of 3,000 mPa·s or more and 10,000 mPa·s or less.

2. The composition according to claim 1, wherein the content of the a) component is from 0.02 to 0.1 mass % as per a total mass of the composition.

3. The composition according to claim 1, wherein the a) component refers to a cellulose hydrophobically modified with long-chain alkyl.

4. The composition according to claim 1, wherein the composition has either of the following characteristics:
   when the composition is subjected to a rolling test carried out at 45 r/min for 4 h, the viscosity of the composition measured at the end of the test decreases by less than 10%, as compared with the initial viscosity thereof; and
   when the composition is subjected continuously to a rolling test carried out at 45 r/min for 4 h and a vibration test carried out at a frequency of 270 times/min for 20 min, the viscosity of the composition measured at the end of the test decreases by less than 20%, as compared with the initial viscosity thereof.

5. A cosmetic, wherein the cosmetic comprises:
   a) cellulose with a hydrophobic group;
   b) a surfactant;
   c) a higher alcohol;
   d) an oil component;
   e) water;
   and optionally, f) a humectant, and/or g) a higher fatty acid;
   the composition has a viscosity of 3,000 mPa·s or more and 10,000 mPa·s or less.

6. The cosmetic according to claim 5, wherein the content of the a) component is from 0.02 to 0.1 mass % as per a total mass of the composition.

7. The cosmetic according to claim 5, wherein the a) component refers to a cellulose hydrophobically modified with long-chain alkyl.

8. The cosmetic according to claim 7, wherein the alkyl has 12 to 22 carbon atoms.

9. The cosmetic according to claim 5, wherein the composition has either of the following characteristics:
   when the composition is subjected to a rolling test carried out at 45 r/min for 4 h, the viscosity of the composition measured at the end of the test decreases by less than 10%, as compared with the initial viscosity thereof; and
   when the composition is subjected continuously to a rolling test carried out at 45 r/min for 4 h and a vibration test carried out at a frequency of 270 times/min for 20 min, the viscosity of the composition measured at the end of the test decreases by less than 20%, as compared with the initial viscosity thereof.

10. The cosmetic according to claim 5, wherein the a) component refers to a hydrophobically modified cellulose having a kinematic viscosity of greater than 120 $mm^2/s$.

11. The composition according to claim 1, wherein the a) component refers to a hydrophobically modified cellulose having a kinematic viscosity of greater than 120 $mm^2/s$.

12. The composition according to claim 3, wherein the alkyl has 12 to 22 carbon atoms.

13. The composition according to claim 1, wherein the viscosity of the composition is from 4,000 to 9,000 mPa·s.

14. The cosmetic according to claim 5, wherein the viscosity of the cosmetic is from 4,000 to 9,000 mPa·s.

* * * * *